(12) United States Patent
Thompson et al.

(10) Patent No.: US 8,900,353 B2
(45) Date of Patent: Dec. 2, 2014

(54) OXYGEN CONCENTRATOR SYSTEM

(71) Applicant: Oxus America, Inc., Rochester Hills, MI (US)

(72) Inventors: Loren M. Thompson, Lapeer, MI (US); Gary C. Abusamra, Rochester Hills, MI (US); Andrew M. Voto, Clarkston, MI (US)

(73) Assignee: Oxus America, Inc., Rochester Hills, MI (US)

( * ) Notice: Subject to any disclaimer, the term of this patent is extended or adjusted under 35 U.S.C. 154(b) by 114 days.

(21) Appl. No.: 13/768,504

(22) Filed: Feb. 15, 2013

(65) Prior Publication Data

US 2013/0213234 A1  Aug. 22, 2013

Related U.S. Application Data

(60) Provisional application No. 61/601,261, filed on Feb. 21, 2012.

(51) Int. Cl.
| | | |
|---|---|---|
| *B01D 53/02* | (2006.01) | |
| *A61M 16/10* | (2006.01) | |
| *B01D 53/047* | (2006.01) | |
| *C01B 13/02* | (2006.01) | |

(52) U.S. Cl.
CPC ........... *B01D 53/0476* (2013.01); *A61M 16/10* (2013.01); *B01D 53/047* (2013.01); *A61M 2209/086* (2013.01); *C01B 13/0259* (2013.01); *A61M 16/101* (2013.01); *A61M 2205/8206* (2013.01); *C01B 13/027* (2013.01)
USPC .................. 96/108; 128/204.18; 128/204.21; 128/204.22; 128/204.23; 128/204.25

(58) Field of Classification Search
USPC ............. 96/108; 128/204.18, 204.21, 204.22, 128/204.23, 204.25
See application file for complete search history.

(56) References Cited

U.S. PATENT DOCUMENTS

| | | | |
|---|---|---|---|
| 6,095,138 | A | 8/2000 | Hognelid et al. |
| 6,346,139 | B1 | 2/2002 | Czabala |
| 6,478,857 | B2 | 11/2002 | Czabala |
| 7,273,051 | B2 | 9/2007 | Whitley et al. |

(Continued)

FOREIGN PATENT DOCUMENTS

| | | |
|---|---|---|
| EP | 1 568 391 | 8/2005 |
| WO | 2010073140 | 7/2010 |

OTHER PUBLICATIONS

European Patent Office, International Search Report and Written Opinion of the International Searching Authority, May 24, 2013.

*Primary Examiner* — Christopher P Jones
(74) *Attorney, Agent, or Firm* — Young Basile Hanlon & MacFarlane P.C.

(57) ABSTRACT

An oxygen concentrator system includes a portable unit and a base unit. The portable unit includes an air separation device. The base unit includes a vacuum pump. The portable unit is moveable with respect to the base unit between a connected position, in which the vacuum pump of the base unit is connected to the air separation device of the portable unit for applying vacuum pressure at the air separation device of the portable unit, and a disconnected position, in which the vacuum pump is not connected to the air separation device of the portable unit. The air separation device operates using a vacuum pressure swing adsorption (VPSA) cycle when the portable unit is in the connected position. The air separation device operates using a pressure swing adsorption (PSA) cycle when the portable unit is in the disconnected position.

20 Claims, 3 Drawing Sheets

(56) References Cited

U.S. PATENT DOCUMENTS

| | | |
|---|---|---|
| 7,350,521 B2 | 4/2008 | Whitley et al. |
| 2002/0053286 A1 | 5/2002 | Czabala |
| 2005/0072426 A1 | 4/2005 | Deane et al. |
| 2005/0161043 A1 | 7/2005 | Whitley et al. |
| 2005/0183572 A1 | 8/2005 | Keefer et al. |
| 2008/0202508 A1 | 8/2008 | McClain et al. |
| 2010/0051030 A1 | 3/2010 | Richard et al. |

OXYGEN CONCENTRATOR SYSTEM

CROSS-REFERENCE TO RELATED APPLICATIONS

This application claims the benefit of U.S. Provisional Application No. 61/601,261, filed Feb. 21, 2012.

TECHNICAL FIELD

The present invention relates to oxygen concentrator systems having a portable portion that can be connected and disconnected with respect to a base portion.

BACKGROUND

Oxygen concentrator systems generate substantially pure (e.g., 82-96% pure) oxygen gas using ambient air as an input gas. Oxygen concentrator systems are commonly used for medical applications by patients who have a need for substantially pure oxygen.

Portable oxygen concentrators typically output a volume of oxygen that is lower than what is output by non-portable oxygen concentrators. The oxygen output of portable units is sometimes not sufficient to meet the demands of some users. For example, some users require a higher amount of oxygen at night when they are sleeping. The size and weight of oxygen concentrators that are able to meet this type of demand tend to be too large and/or heavy to be portable.

SUMMARY

Oxygen concentrator systems are taught herein.

One aspect of the disclosed embodiments is an oxygen concentrator system that includes a portable unit and a base unit. The portable unit includes an air separation device. The base unit includes a vacuum pump. The portable unit is moveable with respect to the base unit between a connected position, in which the vacuum pump of the base unit is connected to the air separation device of the portable unit for applying vacuum pressure at the air separation device of the portable unit, and a disconnected position, in which the vacuum pump is not connected to the air separation device of the portable unit. The air separation device operates using a vacuum pressure swing adsorption (VPSA) cycle when the portable unit is in the connected position. The air separation device operates using a pressure swing adsorption (PSA) cycle when the portable unit is in the disconnected position.

Another aspect of the disclosed embodiments is an oxygen concentrator system that includes a portable unit and a base unit. The portable unit includes an air separation device, a compressor coupled to the air separation device for supplying compressed air to the air separation device, a product gas outlet coupled to the air separation device for receiving a product gas from the air separation device, and a first vacuum port coupled to the air separation device. The base unit includes a second vacuum port and a vacuum pump coupled to the second vacuum port for applying vacuum pressure at the second vacuum port. The portable unit is moveable with respect to the base unit between a connected position, in which the first vacuum port is connected to the second vacuum port, and a disconnected position, in which the first vacuum port is not connected to the second vacuum port. The air separation device operates using a vacuum pressure swing adsorption cycle when the portable unit is in the connected position. The air separation device operates using a pressure swing adsorption cycle when the portable unit is in the disconnected position.

Another aspect of the disclosed embodiments is an oxygen concentrator system that includes a portable unit and a base unit. The portable unit includes an air separation device. The portable unit is moveable with respect to the base unit between a connected position and a disconnected position. The air separation device operates using a vacuum pressure swing adsorption cycle when the portable unit is in the connected position. The air separation device operates using a pressure swing adsorption cycle when the portable unit is in the disconnected position.

BRIEF DESCRIPTION OF THE DRAWINGS

The various features, advantages and other uses of the present apparatus will become more apparent by referring to the following detailed description and drawing in which.

DETAILED DESCRIPTION

Figure 1:
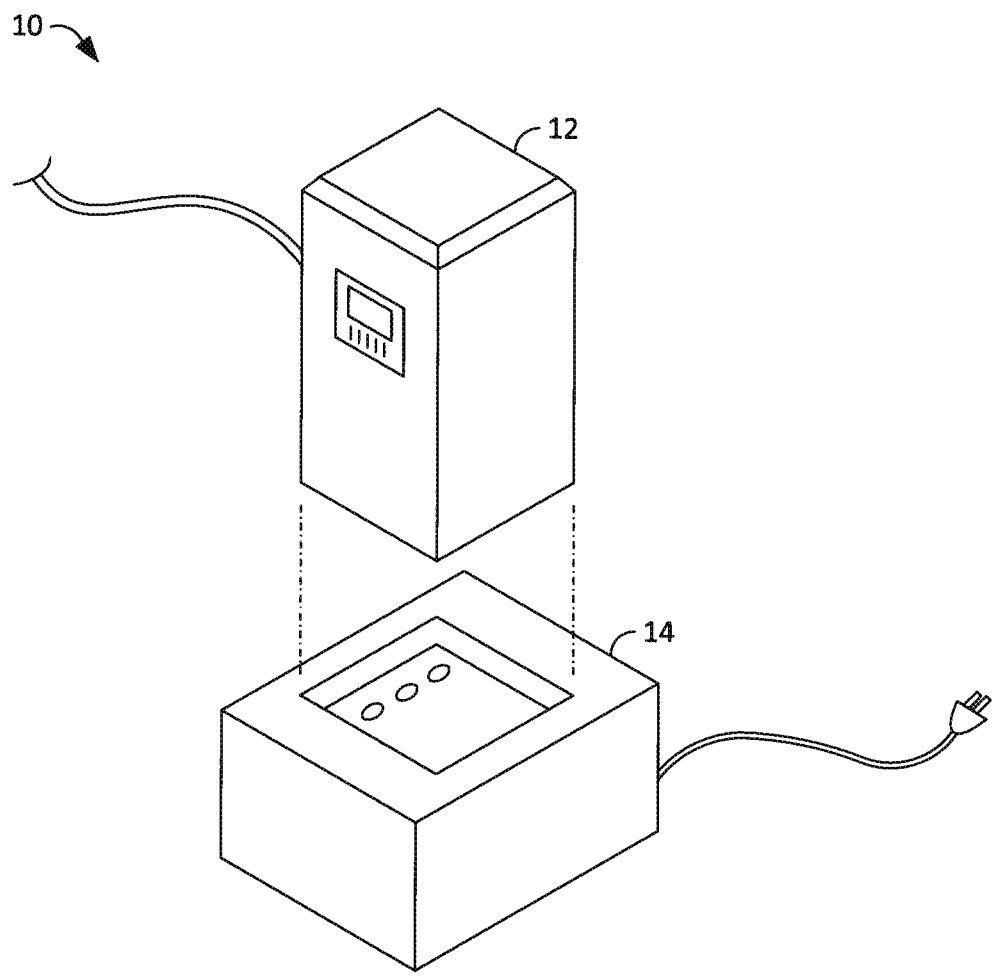
FIG. 1 is an illustration showing an oxygen concentrator system including a portable unit and a base unit.

FIG. 1 shows an oxygen concentrator system 10. The oxygen concentrator system 10 includes a portable unit 12 and a base unit 14. In some implementations, the base unit 14 is non-transportable, meaning that it has a size, weight, configuration or power supply requirement that makes using the base unit while it is being transported difficult. It should be noted, however, that the base unit can also be a portable unit.

As will be described in detail herein, the portable unit 12 is moveable between a connected position and a disconnected position with respect to the base unit 14. The base unit 14 includes at least one component that is configured to be connected to the portable unit 12 when the portable unit 12 is in the connected position with respect to the base unit 14. As an example, the oxygen concentrator system can operate using a vacuum pressure swing adsorption (VPSA) cycle that is facilitated by components that are included in the base unit 14 when the portable unit 12 is in the connected unit with respect to the base unit 14. In the disconnected position, the portable unit 12 can operate independently of the base unit 14, and the oxygen concentrator system 10 can operate using a pressure swing adsorption (PSA) cycle. When the portable unit 12 is used independently of the base unit 14, it can be easily transported and used while in transit. When the portable unit 12 is used in conjunction with the base unit 14, operational characteristics of the combined unit can be improved relative to the operational characteristics of the portable unit alone. For example, in some implementations, the flow rate of a product gas of the oxygen concentrator system 10 can be increased when the portable unit 12 is connected to the base unit 14.

The portable unit 12 and the base unit 14 can be implemented in a variety of physical configurations. The portable unit 12 is configured such that it can be easily transported by a patient, and can be used while it is being transported. Thus, the size, shape, and weight of the portable unit 12 are selected to allow easy transportation. As examples the portable unit 12 can be configured to be carried as a backpack, with a shoulder strap, using a wheeled cart, or by attachment to a wheelchair or other mobility aid. In some implementations, the base unit 14 is generally not meant to be used while the patient is ambulatory, but can have a shape, size, and weight that does allow for transport by a user, for example, in their luggage for travel use. In other implementations, the base unit 14 can be transportable and can be used while the patient is ambulatory, but using the portable unit 12 alone provides advantages of reduced weight and size relative to using the portable unit 12 in combination with the base unit 14. The portable unit 12 can connect to the base unit 14 in a "dock" style arrangement (as illustrated), by connection of pneumatic hoses and optionally electrical and control connections between the two units, or in any other manner.

Figure 2:
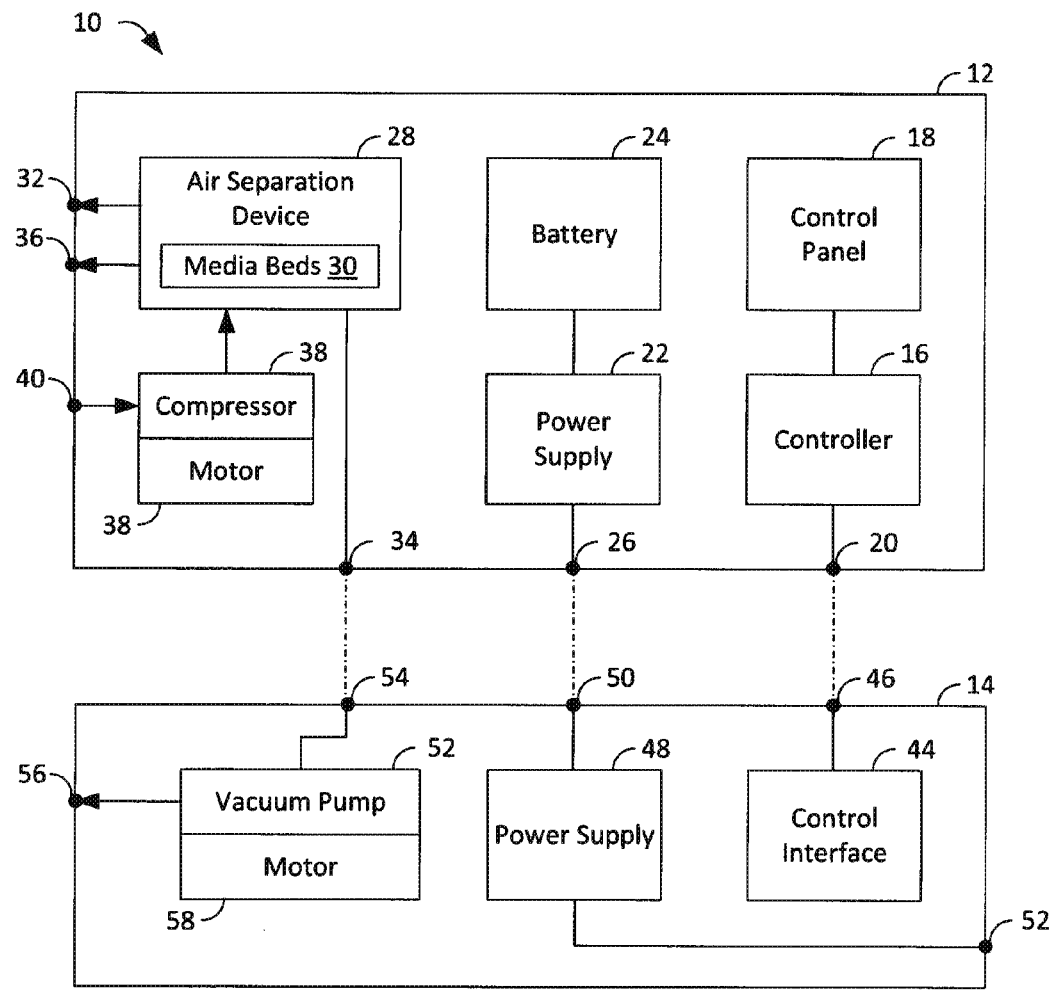
FIG. 2 is a block diagram of the oxygen concentrator system.

As shown in FIG. 2, the portable unit can include a controller 16 and a control panel 18. The controller 16 can be operable to regulate operation of the portable unit 12 of the oxygen concentrator system 10. In some implementations, the controller 16 is also operable to regulate operation of the base unit 14 of the oxygen concentrator system 10. In other implementations, the controller 16 does not control the base unit 14, and instead, the base unit 14 can include its own control system, such as by including a programmable controller, a mechanical control system, a pneumatic control system, or any combination of such systems.

The control panel 18 can be in electrical communication with the controller 16. The control panel 18 can include one or more control elements, switches, buttons, displays, or other hardware components that are mounted to an exterior surface of the portable unit 12 to allow user manipulation of one or more operating parameters of the oxygen concentrator system 10. For example, the control panel 18 can include components that allow a user to start or stop operation of the oxygen concentrator system 10, adjust parameters of its operation, or receive information pertaining to operation of the oxygen concentrator system 10.

The controller 16 can be in electrical communication with a portable-side control connector 20. The portable-side control connector 20 allows the controller 16 of the portable unit 12 to electrically connect to one or more components of the base unit 14 when the portable unit 12 is in a connected position with respect to the base unit 14, as will be described in detail herein.

The portable unit 12 can include a power supply 22 and a battery 24. The power supply 22 is operable to regulate power distribution and consumption by the portable unit 12 and can also be operable to regulate recharging of the battery 24. The battery 24 can be a rechargeable battery of any type that allows operation of one or more electrical components of the portable unit 12 when it is in a disconnected position with respect to the base unit 14. It should be noted that functions such as battery recharging need not be implemented by the portable unit 12, and can, in some implementation, be implemented externally.

The power supply 22 can be in electrical communication with a portable-side power connector 26 is operable to be electrically-connected to the base unit 14 for transmission of electrical power from the base unit 14 to the portable unit 12 when the portable unit 12 is in a connected position with respect to the base unit 14. In other implementations, the power supply 22 is not dependent upon connection to the base unit 14, and the portable-side power connector 26 can be omitted. For example, the power supply 22 can be directly connectable to an external AC or DC power source.

The portable unit 12 includes an air separation device 28. The air separation device 28 is operable to receive air as an input gas and separate the air into constituent components. In particular, the air separation device 28 can be operable to generate a product gas that is substantially pure oxygen. The substantially pure oxygen generated by the air separation device 28 has a much higher oxygen concentration than ambient air. As an example, the substantially pure oxygen that is generated by the air separation device can be approximately 82-96% oxygen. The air separation device 28 also produces wasted gas comprised primarily of nitrogen, as well as other components of the ambient air that are not included in the product gas. The air separation device can utilize an adsorbent material to separate oxygen from ambient air. The air separation device 28 can include one or more adsorbent media beds 30 that each includes an adsorbent material. In some implementations, the adsorbent material is a zeolite material.

The air separation device can be coupled to a product gas outlet port 32 for supplying the product gas to the product gas outlet port 32. The product gas outlet port 32 may be referred to herein as a cannula port.

The air separation device can be coupled to a portable-side vacuum port 34. The portable-side vacuum port 34 can be in fluid communication with the adsorbent media beds 30. As will be described herein, vacuum pressure can be applied at the portable-side vacuum port 34 in order to apply vacuum pressure to the adsorbent media beds 30.

The air separation device 28 can be in communication with a waste gas outlet port 36 for receiving a waste gas from the air separation device 28. The waste gas outlet port 36 can be in fluid communication with the adsorbent media beds 30. In some implementations, the waste gas outlet port 36 can be omitted, and waste gas can be communicated via the portable-side vacuum port 34 using positive pressure or ambient pressure when the air separation device 28 is operated using a pressure swing adsorption cycle.

The air separation device 28 is in fluid communication with the positive pressure outlet side of a compressor 38. The compressor 38 is in fluid communication with an air intake port 40 and is in fluid communication with the adsorbent media beds 30 of the air separation device 28. Ambient air is received at the air intake port 40 and is compressed by the compressor 38 before it is delivered to the adsorbent media beds 30. In some implementations, the compressor 38 is operable to compress ambient air to a pressure between 7 and 40 psig before the compressed air is delivered to the adsorbent media beds 30 of the air separation device 28. The compressor 38 can be operably connected to a motor 42. The motor 42 can be an electric motor is mechanically coupled to the compressor 38 for delivering a rotational output to the compressor 38 that drives operation of the compressor 38.

The air separation device 28 can include a valve assembly (not shown) that is operable to open and close fluid communication between the adsorbent media beds 30 of the air separation device 28 with respect to the product gas outlet port 32, the portable-side vacuum port 34, the waste gas outlet port 36, and the compressor 38. The valve assembly can be an electrically-operated or solenoid operated valve assembly that is controlled by the controller 16. Other types of valve assemblies can be utilized. In addition to controlling the valve assembly of the air separation device 28, the controller 16 can also control operation of other aspects of the air separation device 28 and can control operation of the compressor 38, the motor 42, the power supply 22, and the battery 24, as well as any other systems that are incorporated in the portable unit 12.

The base unit 14 can include a control interface 44 that is in electrical connection with a base-side control connector 46. The base-side control connector 46 can be electrically-connected and disconnected with respect to the portable-side control connector 20. When the base-side control connector 46 and the portable-side control connector 20 are electrically connected, electrical communications are established between the controller 16 and the control interface 44. This allows signals and/or data to be passed between the controller 16 and the control interface 44. As one example, the control interface 44 can be a programmable controller that is operable to control systems and components that are part of the base unit 14. In this example, aspects of the control exercised by the control interface 44 can be set by the controller 16. It should be understood, however, that the functions of the controller 16 of the control interface 44 could be reversed, and in such an example, the control panel 18 could be incorporated in the base unit 14 such that it is in electrical communication directly with the control interface 44. In another implementation, the control interface 44 is a wiring harness that is operable to couple the controller 16 to various systems and elements that are part of the base unit 14 when the portable unit 12 is connected to the base unit 14. The base unit 14 can also include a power supply 48. The power supply 48 can be in electrical connection with a base-side power connector 50. The base-side power connector 50 is electrically connectable to the portable-side power connector 26 of the portable unit 12. Thus, when the portable unit 12 is connected to the base unit 14, electrical communication is established between the power supply 22 and the power supply 48. In one example, the power supply 48 is operable to receive AC power from the base-side power connector 50 of the base unit 14 and is operable to supply AC power to systems and components of the base unit 14, as well as systems and components of the portable unit 12 via the power supply 22 of the portable unit 12. In another implementation, the power supply 48 can include an AC/DC converter that produces DC power from AC power and supplies DC power to either or both of the base unit 14 and the portable unit 12 via the power supply 22 thereof.

The base unit 14 includes a vacuum pump 52 that is coupled to a base-side vacuum port 54 for applying vacuum pressure at the base-side vacuum port 54. The vacuum pump 52 can also be coupled to an exhaust gas outlet port 56 for expelling gas from the vacuum pump 52. The vacuum pump 52 can have any configuration now known or later devised that is operable to apply vacuum pressure at the base-side vacuum port 54. The vacuum pump 52 can be driven by a motor 58. In some implementations, the motor 58 is an electrically-operated motor that is mechanically connected to the vacuum pump 52 by, for example, a rotational output shaft of the motor 58.

The base-side vacuum port 54 is connectable and disconnectable with respect to the portable-side vacuum port 34. The connection can be a direct connection or an indirect connection. An example of a direct connection is coupling of pneumatic connectors that are formed on each of the portable unit 12 and the base unit 14. An example of indirect connection is coupling the base-side vacuum port 54 to the portable-side vacuum port 34 via a hose. When the portable unit 12 is in a connected position with respect to the base unit 14, a pneumatic coupling is defined between the portable unit 12 and the base unit 14 by the portable-side vacuum port 34 and the base-side vacuum port 54. In a connected position, the vacuum pump 52 is operable to apply vacuum pressure to the adsorbent media beds 30 of the air separation device 28 via the portable-side vacuum port 34 and the base-side vacuum port 54. The portable-side vacuum port 34 and the base-side vacuum port 54 can cooperate to define the only fluid transmitting coupling between the portable unit 12 and the base unit 14.

The portable unit 12 can operate independent of the base unit 14 when the portable unit 12 is in the disconnected position with respect to the base unit 14. In the disconnected position, the portable-side control connector 20, the portable-side power connector 26, and the portable-side vacuum port 34 of the portable unit 12 are disconnected with respect to the base-side control connector 46, the base-side power connector 50, and the base-side vacuum port 54 of the base unit 14, respectively. When the portable unit 12 is operated independent of the base unit 14, it can be operated using the pressure swing adsorption cycle. In the pressure swing adsorption cycle, compressed air is supplied from the compressor 38 to one of the adsorbent media beds 30 of the air separation device 28 in order to pressurize the adsorbent media bed. When the adsorbent media bed 30 is pressurized, the nitrogen and, optionally, other non-oxygen components of the compressed air are adsorbed by the zeolite material or other adsorbent material that is contained within the adsorbent media beds 30. The valve assembly of the air separation device 28 then vents the adsorbent media bed 30 to the product gas outlet port 32, thereby supplying substantially pure oxygen to the product gas outlet port 32. Connection of the adsorbent media beds 30 to the product gas outlet port 32 is then closed, and waste gas is expelled from the adsorbent media beds 30 at ambient pressure or by positive pressure using product gas that is delivered from another one of the adsorbent media beds 30. The adsorbent media beds 30 can be vented by connection to the waste gas outlet port 36, or to another outlet path that is in communication with atmosphere such as the portable-side vacuum port 34, which can be operable to vent gas to atmosphere when it is not connected to the base unit 14. The pressure swing adsorption cycle can then be repeated. When the portable unit 12 is connected to the base unit 14, the oxygen concentrator system 10 can be operated using a vacuum pressure swing adsorption cycle. In the connected position of the portable unit 12 with respect to the base unit 14, the portable-side control connector 20, the portable-side power connector 26, and the portable-side vacuum port 34 of the portable unit 12 are coupled to the base-side control connector 46, the base-side power connector 50, and the base-side vacuum port 54 of the base unit 14, respectively.

In the vacuum pressure swing adsorption cycle, compressed air is supplied from the compressor 38 to one of the adsorbent media beds 30 to pressurize the media bed. Product gas is then delivered by establishing fluid communication between the adsorbent media bed 30 and the product gas outlet port 32. Once the product gas has been expelled from the adsorbent media bed 30, fluid communication with the product gas outlet port 32 is closed, and fluid communication is established between the vacuum pump 52 and the adsorbent media bed 30 of the air separation device 28 via the portable-side vacuum port 34 and the base-side vacuum port 54. The vacuum pump 52 applies vacuum pressure to the adsorbent media bed 30 and expels the waste gas at the exhaust gas outlet port 56.

Operation of the oxygen concentrator system 10 in the VPSA cycle when the portable unit 12 is connected to the base unit 14 can increase the oxygen output of the oxygen concentrator system 10, as opposed to independent operation of the portable unit 12. As an example, when the portable unit 12 is operated independently using the PSA cycle, an oxygen output of approximately two liters per minute can be delivered at the product gas outlet port 32. When the portable unit 12 is connected to the base unit 14 and the oxygen concentrator system 10 is operated using the vacuum pressure swing adsorption cycle, approximately three liters per minute of oxygen can be delivered at the product gas outlet port 32. The ability of the portable unit 12 to operate independently, however, allows it to be transportable without the added weight of the components in the base unit 14. In the implementation described herein, connection of the portable unit 12 to the base unit 14 can be accomplished with a single fluid coupling between the portable unit 12 and the base unit 14, thereby reducing the complexity of connecting the portable unit 12 with respect to the base unit 14.

In an alternative example, the control interface 44 of the base unit 14 can be omitted. In this example, the base unit 14 is provided with alternative means for detecting the presence, connection, and or operation of the portable unit 12 with respect to the base unit 14. For example, the base unit 14 can include a detector that is operable to detect connection of the base-side vacuum port 54 with respect to the portable-side vacuum port 34. This detector can be a pneumatic detector that is operable to sense a pressure condition at the base-side vacuum port 54. This detector could alternatively be a mechanical switch, a magnetic switch, or any other means.

Figure 3:
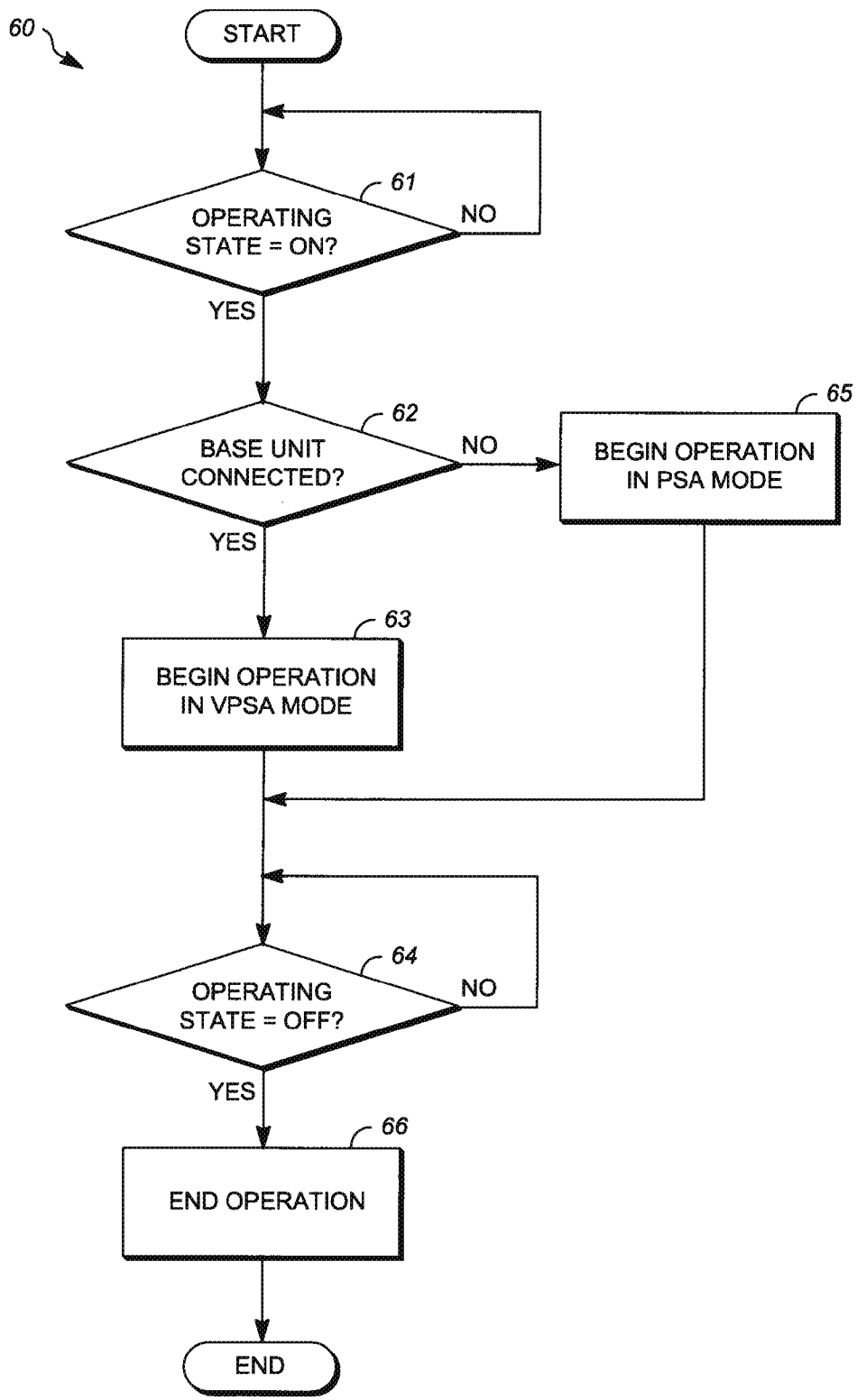
FIG. 3 is a flow chart showing operation of the oxygen concentrator system.

FIG. 3 is a flow chart showing a process 60 for operation of the oxygen concentrator system 10. The operations described in this flow chart can be implemented in the form of computer software instructions, hardware based control systems, or mechanical based control systems that regulate operation of the oxygen concentrator system 10. In one implementation, this process is implemented as software that is embodied in computer executable instructions that are stored in a tangible media, such as memory at the controller 16, and those instructions are executable by the controller 16 to perform the functions that will be described with respect to FIG. 3.

The process 60 can begin at step 61, where a determination is made regarding the requested operating state of the oxygen concentrator system 10. If operation of the oxygen concentrator system 10 has been requested, such as by user input, it is determined that the operating state of the unit is "on," and the process proceeds to step 62. Otherwise, the process returns to step 61 until such time as the operation of the unit is requested.

At step 62, a determination is made as to whether the portable unit 12 is connected to the base unit 14. If the portable unit 12 is connected to the base unit 14, the process proceeds to step 63, where the controller 16 determines that the oxygen concentrator system begins operating in VPSA mode, using the vacuum pump 52 of the base unit 14, and the process continues to step 64. If, at step 62, it is determined that the portable unit 12 is not connected to the base unit 14, the process proceeds to step 65, where the controller 16 determines that the oxygen concentrator system 10 is to be operated in PSA mode. The process then advances to step 64. At step 64, operation in the current mode is continued until it is determined that operation of the oxygen concentrator is no longer required, such as in response to user input, and that the requested operating state of the unit is now "off." If the operating state has not changed, step 64 can be repeated until such time as the operating state changes. In response to determining that a requested operating state of the unit is now "off," operation of the unit is ended at step 66. Otherwise, the process returns to step 61.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An oxygen concentrator system, comprising:
   a portable unit including an air separation device; and
   a base unit including a vacuum pump, wherein the portable unit is moveable with respect to the base unit between a connected position, in which the vacuum pump of the base unit is connected to the air separation device of the portable unit for applying vacuum pressure at the air separation device of the portable unit, and a disconnected position, in which the vacuum pump is not connected to the air separation device of the portable unit, and the air separation device operates using a vacuum pressure swing adsorption cycle when the portable unit is in the connected position, and the air separation device operates using a pressure swing adsorption cycle when the portable unit is in the disconnected position.

2. The oxygen concentrator system of claim 1, wherein the air separation device includes at least one sieve bed having an adsorbent material disposed therein.

3. The oxygen concentrator system of claim 1, wherein the portable unit includes a first vacuum port in communication with the air separation device, and the base unit includes a second vacuum port in communication with the vacuum pump, wherein the first vacuum port is connected to the second vacuum port when the portable unit is in the connected position.

4. The oxygen concentrator system of claim 3, wherein the first vacuum port and the second vacuum port cooperate to define the only fluid-transmitting coupling between the portable unit and the base unit.

5. The oxygen concentrator system of claim 1, further comprising:
   a detector that is operable to determine whether the portable unit is in the connected position or the disconnected position.

6. The oxygen concentrator system of claim 5, wherein the detector is located in the base unit.

7. The oxygen concentrator system of claim 6, wherein the detector is a pneumatic detector.

8. The oxygen concentrator system of claim 7, wherein the pneumatic detector is operable to sense a pressure condition.

9. An oxygen concentrator system, comprising:
   a portable unit including an air separation device, a compressor coupled to the air separation device for supplying compressed air to the air separation device, a product gas outlet coupled to the air separation device for receiving a product gas from the air separation device, and a first vacuum port coupled to the air separation device; and
   a base unit including a second vacuum port and a vacuum pump coupled to the second vacuum port for applying vacuum pressure at the second vacuum port,
   wherein the portable unit is moveable with respect to the base unit between a connected position, in which the first vacuum port is connected to the second vacuum port, and a disconnected position, in which the first vacuum port is not connected to the second vacuum port, and the air separation device operates using a vacuum pressure swing adsorption cycle when the portable unit is in the connected position, and the air separation device operates using a pressure swing adsorption cycle when the portable unit is in the disconnected position.

10. The oxygen concentrator system of claim 9, wherein the air separation device includes at least one sieve bed having an adsorbent material disposed therein.

11. The oxygen concentrator system of claim 9, wherein the vacuum pump of the base unit is operable to apply vacuum pressure to the air separation device when the air separation device operates using the vacuum pressure swing adsorption cycle.

12. The oxygen concentrator system of claim 9, wherein the first vacuum port and the second vacuum port cooperate to define the only fluid-transmitting coupling between the portable unit and the base unit.

13. The oxygen concentrator system of claim 9, further comprising:
a detector that is operable to determine whether the portable unit is in the connected position or the disconnected position.

14. The oxygen concentrator system of claim 13, wherein the detector is located in the base unit.

15. The oxygen concentrator system of claim 14, wherein the detector is a pneumatic detector.

16. The oxygen concentrator system of claim 15, wherein the pneumatic detector is operable to sense a pressure condition at the second vacuum port.

17. An oxygen concentrator system, comprising:
a portable unit including an air separation device; and
a base unit, wherein the portable unit is moveable with respect to the base unit between a connected position and a disconnected position, wherein the air separation device operates using a vacuum pressure swing adsorption cycle when the portable unit is in the connected position, and the air separation device operates using a pressure swing adsorption cycle when the portable unit is in the disconnected position.

18. The oxygen concentrator system of claim 17, wherein the base unit includes at least one component that is configured to be connected to the portable unit when the portable unit is in the connected position with respect to the base unit.

19. The oxygen concentrator system of claim 17, wherein the at least one component of the base unit is a vacuum pump that is operable to supply vacuum pressure to the air separation device of the portable unit when the portable unit is in the connected position with respect to the base unit.

20. The oxygen concentrator system of claim 19, wherein the vacuum pump is operable to apply vacuum pressure to the air separation device when the air separation device operates using the vacuum pressure swing adsorption cycle.

\* \* \* \* \*